United States Patent
Kulkarni et al.

(10) Patent No.: US 9,814,517 B2
(45) Date of Patent: *Nov. 14, 2017

(54) DEPLOYMENT MECHANISMS FOR MULTI-FUNCTION SURGICAL INSTRUMENTS

(71) Applicant: COVIDIEN LP, Mansfield, MA (US)

(72) Inventors: Abhijit G. Kulkarni, Andhra Pradesh (IN); Amarsinh D. Jadhav, Islampur-Dist-Sangli (IN); Thiyagarajan Chelladurai, Tiruppur (IN)

(73) Assignee: COVIDIEN LP, Mansfield, MA (US)

( * ) Notice: Subject to any disclaimer, the term of this patent is extended or adjusted under 35 U.S.C. 154(b) by 431 days.

This patent is subject to a terminal disclaimer.

(21) Appl. No.: 14/543,291

(22) Filed: Nov. 17, 2014

(65) Prior Publication Data
US 2016/0135871 A1    May 19, 2016

(51) Int. Cl.
A61B 18/12 (2006.01)
A61B 18/14 (2006.01)
(Continued)

(52) U.S. Cl.
CPC .......... *A61B 18/1445* (2013.01); *A61B 17/29* (2013.01); *A61B 17/2909* (2013.01);
(Continued)

(58) Field of Classification Search
CPC . A61B 17/29; A61B 17/2909; A61B 18/1442; A61B 18/1445; A61B 18/1447;
(Continued)

(56) References Cited

U.S. PATENT DOCUMENTS 5,312,391 A   5/1994   Wilk
5,318,589 A   6/1994   Lichtman
(Continued)

FOREIGN PATENT DOCUMENTS

DE    202007007327 U1   7/2007
EP         2679185 A1   1/2014

OTHER PUBLICATIONS

European search report issued in corresponding application No. EP15191336.5 dated Jan. 11, 2016.

*Primary Examiner* — Daniel Fowler

(57) ABSTRACT

A surgical instrument includes an end effector assembly having first and second jaw members movable between a spaced-apart position and an approximated position. A trigger assembly is movable between an un-actuated position and an actuated position. An energizable member is selectively movable relative to the jaw members between a first storage position and a first deployed position. At least a portion of the energizable member extends distally from the jaw members in the first deployed position. A selector is operably associated with the trigger assembly and the energizable member. The selector is transitionable between a first state, wherein the energizable member is decoupled from the trigger assembly, and a second state, wherein the energizable member is coupled to the trigger assembly such that movement of the trigger assembly from the un-actuated position to the actuated position effects movement of the energizable member from the storage position to the deployed position.

18 Claims, 14 Drawing Sheets

(51) Int. Cl.
   *A61B 17/29* (2006.01)
   *A61B 18/00* (2006.01)
   *A61B 17/00* (2006.01)
(52) U.S. Cl.
   CPC ........... *A61B 2017/00393* (2013.01); *A61B 2018/0063* (2013.01); *A61B 2018/00607* (2013.01); *A61B 2018/00916* (2013.01); *A61B 2018/1422* (2013.01); *A61B 2018/1455* (2013.01); *A61B 2018/1467* (2013.01); *A61B 2018/1475* (2013.01)
(58) Field of Classification Search
   CPC ........... A61B 2017/00393; A61B 2018/00607; A61B 2018/0063; A61B 2018/00916; A61B 2018/1422; A61B 2018/1455; A61B 2018/1467; A61B 2018/145; A61B 2018/1452; A61B 2018/1457
   See application file for complete search history.

(56) References Cited

U.S. PATENT DOCUMENTS

| | | | |
|---|---|---|---|
| 5,324,254 A | 6/1994 | Phillips | |
| 5,401,274 A | 3/1995 | Kusunoki | |
| 5,445,638 A | 8/1995 | Rydell et al. | |
| 5,458,598 A | 10/1995 | Feinberg et al. | |
| 5,556,397 A | 9/1996 | Long et al. | |
| 5,735,873 A | 4/1998 | MacLean | |
| 5,792,164 A | 8/1998 | Lakatos et al. | |
| 5,893,863 A | 4/1999 | Yoon | |
| 5,919,202 A | 7/1999 | Yoon | |
| 5,922,001 A * | 7/1999 | Yoon | A61B 17/12013 606/139 |
| 6,113,596 A | 9/2000 | Hooven et al. | |
| 6,156,009 A | 12/2000 | Grabek | |
| 6,190,386 B1 | 2/2001 | Rydell | |
| 6,270,497 B1 | 8/2001 | Sekino et al. | |
| 6,299,625 B1 | 10/2001 | Bacher | |
| 6,387,094 B1 | 5/2002 | Eitenmuller | |
| 6,409,728 B1 * | 6/2002 | Ehr | A61B 18/1445 606/205 |
| 6,551,313 B1 | 4/2003 | Levin | |
| 6,679,882 B1 | 1/2004 | Kornerup | |
| 6,808,525 B2 | 10/2004 | Latterell et al. | |
| 6,942,662 B2 | 9/2005 | Goble et al. | |
| 7,033,356 B2 | 4/2006 | Latterell et al. | |
| 7,063,699 B2 | 6/2006 | Hess et al. | |
| 7,128,254 B2 | 10/2006 | Shelton, IV et al. | |
| 7,232,440 B2 | 6/2007 | Dumbauld et al. | |
| 7,367,976 B2 | 5/2008 | Lawes et al. | |
| 7,402,162 B2 | 7/2008 | Ouchi | |
| 7,445,621 B2 | 11/2008 | Dumbauld et al. | |
| 7,510,562 B2 | 3/2009 | Lindsay | |
| 7,588,570 B2 | 9/2009 | Wakikaido et al. | |
| 7,658,311 B2 | 2/2010 | Boudreaux | |
| 7,758,577 B2 | 7/2010 | Nobis et al. | |
| 7,815,636 B2 | 10/2010 | Ortiz | |
| 7,819,872 B2 | 10/2010 | Johnson et al. | |
| 8,257,352 B2 | 9/2012 | Lawes et al. | |
| 8,353,437 B2 | 1/2013 | Boudreaux | |
| 2002/0049442 A1 | 4/2002 | Roberts et al. | |
| 2002/0072766 A1 | 6/2002 | Hunt et al. | |
| 2004/0236326 A1 | 11/2004 | Schulze et al. | |
| 2005/0113827 A1 | 5/2005 | Dumbauld et al. | |
| 2005/0187547 A1 | 8/2005 | Sugi | |
| 2008/0215050 A1 | 9/2008 | Bakos | |
| 2009/0125026 A1 | 5/2009 | Rioux et al. | |
| 2009/0125027 A1 | 5/2009 | Fischer | |
| 2009/0131974 A1 | 5/2009 | Pedersen et al. | |
| 2009/0254084 A1 | 10/2009 | Naito | |
| 2010/0185196 A1 | 7/2010 | Sakao et al. | |
| 2010/0185197 A1 | 7/2010 | Sakao et al. | |
| 2010/0292690 A1 | 11/2010 | Livneh | |
| 2011/0087218 A1 | 4/2011 | Boudreaux et al. | |
| 2011/0130757 A1 | 6/2011 | Horlle et al. | |
| 2011/0264093 A1 | 10/2011 | Schall | |
| 2012/0330351 A1 | 12/2012 | Friedman et al. | |
| 2014/0135758 A1 | 5/2014 | Mueller | |
| 2014/0276797 A1 | 9/2014 | Batchelor et al. | |

* cited by examiner

DEPLOYMENT MECHANISMS FOR MULTI-FUNCTION SURGICAL INSTRUMENTS

BACKGROUND

Technical Field

The present disclosure relates to surgical instruments and, more particularly, to deployment mechanisms for deploying, e.g., actuating, one or more components of a surgical instrument.

Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include a trigger for selectively deploying a knife between the jaw members to cut tissue grasped therebetween.

As can be appreciated, as additional functional components are added to the surgical instrument, additional deployment structures or deployment structures capable of actuating more than one component are required. However, multiple deployment structures and/or combined deployment structures may be limited by spatial constraints within the housing of the surgical instrument, functional constraints of the components, e.g., where a combined deployment structure imparts additional force requirements for deploying one or more of the components coupled thereto, and/or may overly complicate the operable components of the surgical instrument.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with the present disclosure, a surgical instrument is provided including an end effector assembly having first and second jaw members. One or both of the jaw members is movable relative to the other between a spaced-apart position and an approximated position for grasping tissue therebetween. A trigger assembly is movable between an un-actuated position and an actuated position. An energizable member is selectively movable relative to the jaw members between a first storage position and a first deployed position. At least a portion of the energizable member extends distally from the jaw members in the first deployed position. A selector assembly is operably associated with the trigger assembly and the energizable member. The selector assembly is transitionable between a first state, wherein the energizable member is decoupled from the trigger assembly, and a second state, wherein the energizable member is coupled to the trigger assembly such that movement of the trigger assembly from the un-actuated position to the actuated position effects movement of the energizable member from the storage position to the deployed position.

In an aspect of the present disclosure, a knife is provided. In such aspects, the knife is selectively movable relative to the jaw members between a retracted position and an extended position. The knife extends at least partially between the jaw members to cut tissue grasped therebetween in the extended position. The knife is coupled to the trigger assembly such that movement of the trigger assembly from the un-actuated position to the actuated position moves the knife from the retracted position to the extended position in both the first and second states of the selector assembly.

In another aspect of the present disclosure, the energizable member is disposed within an insulative groove defined within one of the jaw members in the first storage position, and extends distally from the jaw members in the first deployed position.

In another aspect of the present disclosure, the energizable member is adapted to connect to a source of energy for supplying monopolar energy to tissue.

In yet another aspect of the present disclosure, an insulative sleeve is provided. The insulative sleeve in such aspects is selectively movable relative to the jaw members between a second storage position, wherein the insulative sleeve is positioned proximally of the jaw members, and a second deployed position, wherein the insulative sleeve is disposed about the jaw members. In the first state of the selector assembly, the insulative sleeve is decoupled from the trigger assembly. In the second state of the selector assembly, on the other hand, the insulative sleeve is coupled to the trigger assembly such that movement of the trigger assembly from the un-actuated position to the actuated position effects movement of the insulative sleeve from the second storage position to the second deployed position.

In still another aspect of the present disclosure, the energizable member and the insulative sleeve define equal travel lengths between their respective storage and deployed positions. Alternatively, the energizable member and the insulative sleeve may define different travel lengths between their respective storage and deployed positions. In such aspects where different travel lengths are provided, the energizable member and the insulative sleeve may be configured to move together between the respective storage positions thereof and the deployed position of the energizable member, while the insulative sleeve thereafter moves further to the deployed position of the insulative sleeve.

In still yet another aspect of the present disclosure, the selector assembly includes a selector ring. The selector ring is rotatable between a first orientation corresponding to the first state, and second orientation corresponding to the second state.

In another aspect of the present disclosure, the selector ring is coupled to a hub associated with the energizable member. The hub is displaced from a travel path of a slider of the trigger assembly in the first orientation of the selector ring and intersects the travel path of the slider of the trigger assembly in the second orientation of the selector ring such that the slider is urged into contact with the hub upon actuation of the trigger assembly to move the energizable member from the first storage position to the first deployed position.

In still another aspect of the present disclosure the surgical instrument further includes a housing having a shaft extending distally from the housing with the end effector disposed at a distal end of the shaft. In such aspects, a selector member is disposed on the housing. The selector member is coupled to the selector ring and is movable between a first position and a second position relative to the housing to rotate the selector ring between the first orientation and the second orientation.

In yet another aspect of the present disclosure, a lock assembly configured to lock the energizable member in the first deployed position upon movement of the energizable member to the first deployed position is provided. Further, the lock assembly may be configured to unlock the energizable member from the deployed position in response to transitioning of the selector assembly from the second state back to the first state.

In still yet another aspect of the present disclosure, one or both of the jaw members is adapted to connect to a source of energy for conducting energy through tissue grasped between the jaw members.

Another surgical instrument provided in accordance with the present disclosure includes a housing, a shaft extending distally from the housing, and an end effector assembly disposed at a distal end of the shaft. The end effector assembly includes first and second jaw members movable between a spaced-apart position and an approximated position for grasping tissue therebetween. A trigger assembly is coupled to the housing and includes a trigger movable relative to the housing between an un-actuated position and an actuated position. A deployable assembly including an energizable member and an insulative sleeve is also provided. The deployable assembly is selectively movable relative to the jaw members between a storage position and a deployed position. A selector assembly is operably associated with the trigger assembly and the deployable assembly. The selector assembly includes a selector member coupled to the housing. The selector member is movable relative to the housing between a first position and a second position for transitioning the selector assembly between a first state, wherein the deployable assembly is decoupled from the trigger assembly, and a second state, wherein the deployable assembly is coupled to the trigger assembly such that movement of the trigger assembly from the un-actuated position to the actuated position effects movement of the deployable assembly from the storage position to the deployed position.

In an aspect of the present disclosure, the surgical instrument further includes a knife selectively movable relative to the jaw members between a retracted position and an extended position. In the extended position, the knife extends at least partially between the jaw members to cut tissue grasped therebetween. The knife is coupled to the trigger assembly such that movement of the trigger assembly from the un-actuated position to the actuated position moves the knife from the retracted position to the extended position in both the first and second states of the selector assembly.

In another aspect of the present disclosure, the energizable member and the insulative sleeve define equal travel lengths upon movement of the deployable assembly between the storage position and the deployed position. Alternatively, the energizable member and the insulative sleeve may define different travel lengths upon movement of the deployable assembly between the storage position and the deployed position. In such aspects where different travel lengths are provided, the energizable member and the insulative sleeve may be configured to move together between the respective storage positions thereof and the deployed position of the energizable member, while the insulative sleeve thereafter moves further to the deployed position of the insulative sleeve.

In yet another aspect of the present disclosure, a lock assembly is disposed within the housing. The lock assembly is configured to engage a portion of the deployable assembly upon movement of the deployable assembly to the deployed position. The lock assembly may further be configured to unlock the deployable assembly from the deployed position in response to transitioning of the selector assembly from the second state back to the first state.

A method of surgery is also provided in accordance with the present disclosure. The method includes grasping and cutting tissue, e.g., grasping tissue between first and second jaw members and actuating a trigger assembly to advance a knife between the first and second jaw members to cut tissue grasped therebetween. The method further includes deploying an energizable member and treating tissue therewith, e.g., transitioning a selector assembly from a first state to a second state to couple the trigger assembly to an energizable member, actuating the trigger assembly to deploy the energizable member from a storage position to a deployed position, and selectively energizing the energizable member to treat tissue.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
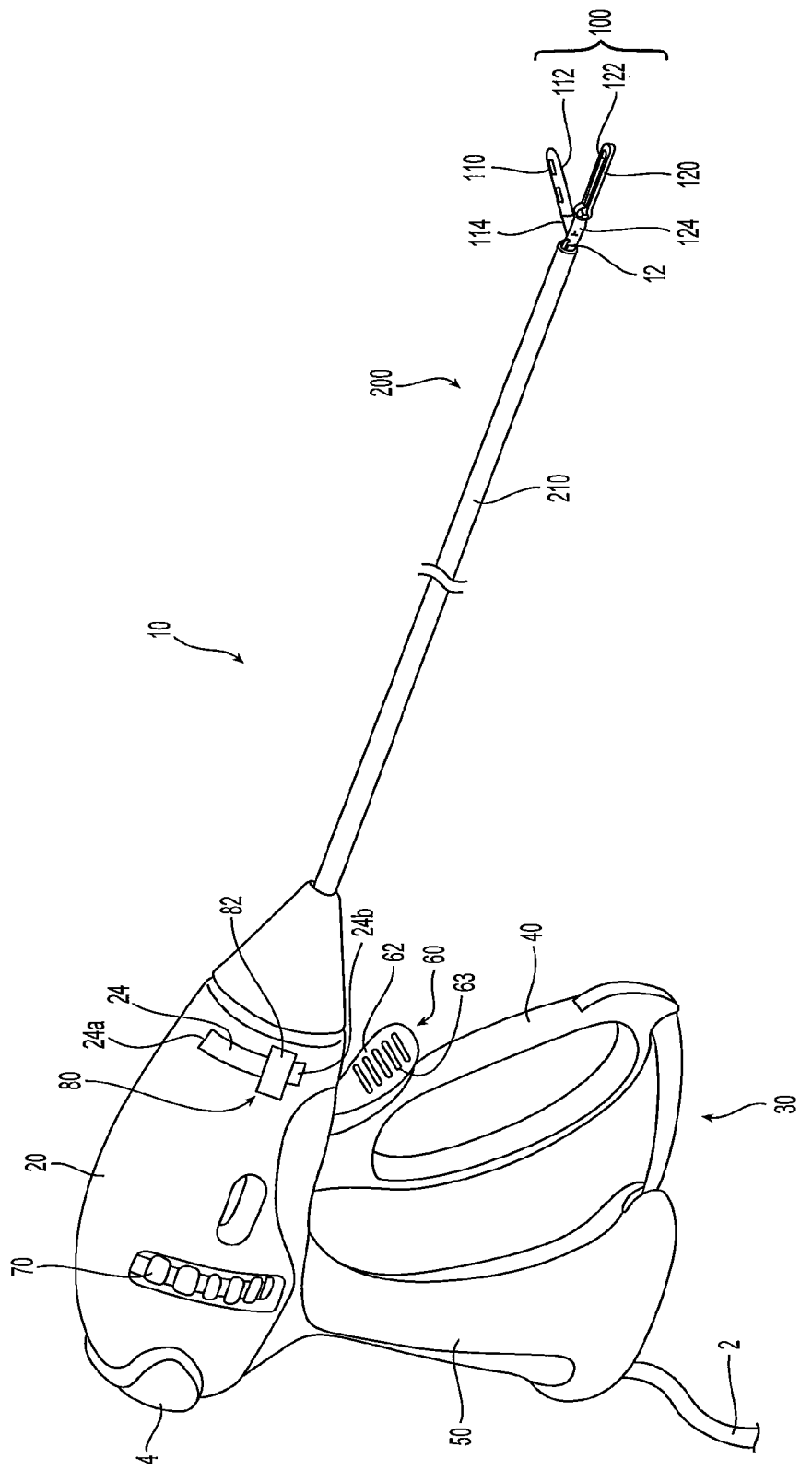
FIG. 1 is a front, perspective view of an endoscopic surgical forceps configured for use in accordance with the present disclosure.

Referring generally to FIG. 1, a forceps provided in accordance with the present disclosure is shown generally identified by reference numeral 10. Forceps 10, as will be described below, is configured to operate in both a bipolar mode, e.g., for grasping, treating, and/or dissecting tissue, and a monopolar mode, e.g., for treating and/or dissecting tissue. Although the present disclosure is shown and described with respect to forceps 10, the aspects and features of the present disclosure are equally applicable for use with any suitable surgical instrument or portion(s) thereof for selectively actuating, moving, and/or deploying the assemblies and/or components of the surgical instrument. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIG. 1, forceps 10 includes a housing 20, a handle assembly 30, a trigger assembly 60, a rotating assembly 70, a selector assembly 80, an end effector assembly 100, and a monopolar assembly 200. Forceps 10 further includes a shaft 12 having a distal end configured to mechanically engage end effector assembly 100 and a proximal end that mechanically engages housing 20. Forceps 10 also includes an electrosurgical cable 2 that connects forceps 10 to a generator (not shown) or other suitable power source, although forceps 10 may alternatively be configured as a battery powered instrument. Cable 2 includes wires (not shown) extending therethrough that have sufficient length to extend through shaft 12 in order to provide electrical energy to at least one electrically-conductive surface 112, 122 (FIG. 2A) of jaw members 110, 120, respectively, of end effector assembly 100, e.g., upon activation of activation switch 4 in a bipolar mode. One or more of the wires (not shown) of cable 2 extends through housing 20 in order to provide electrical energy to monopolar assembly 200, e.g., upon activation of activation switch 4 in a monopolar mode. Rotating assembly 70 is rotatable in either direction to rotate end effector assembly 100 and monopolar assembly 200 relative to housing 20. Housing 20 houses the internal working components of forceps 10, which are described in detail below.

Figure 2A:
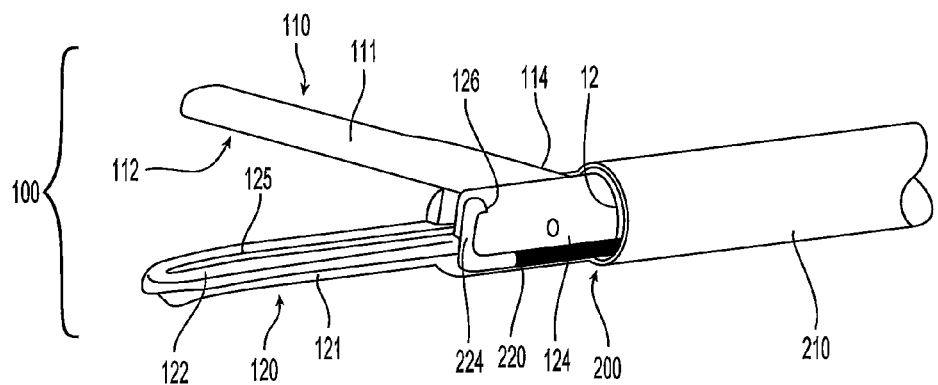
FIG. 2A is an enlarged, front, perspective view of an end effector assembly of the forceps of FIG. 1, wherein jaw members of the end effector assembly are disposed in a spaced-apart position and wherein a monopolar assembly is disposed in a storage position.
Figure 2B:
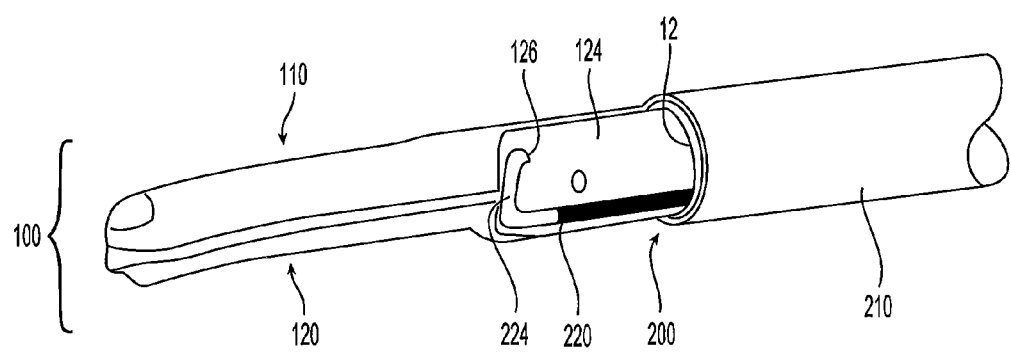
FIG. 2B is an enlarged, front, perspective view of the end effector assembly of FIG. 2A, wherein the jaw members are disposed in an approximated position and wherein the monopolar assembly is disposed in the storage position.
Figure 2C:
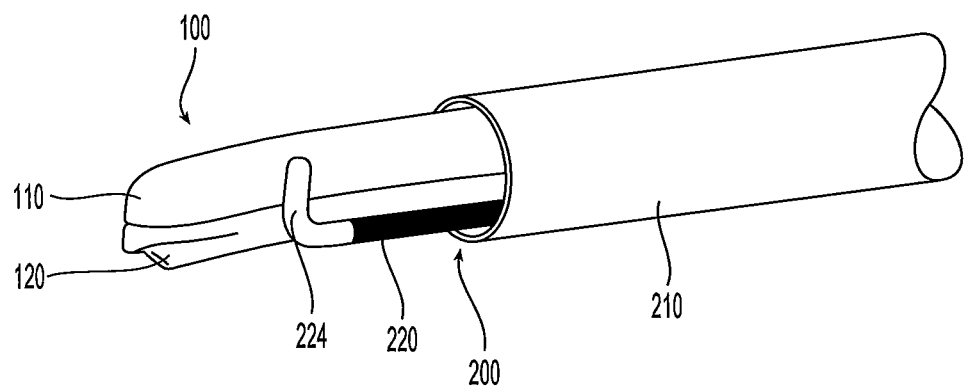
FIG. 2C is an enlarged, front, perspective view of the end effector assembly of FIG. 2A, wherein the jaw members are disposed in the approximated position and wherein the monopolar assembly is transitioning from the storage position to a deployed position.

Referring to FIGS. 2A-2B, end effector assembly 100 is attached at a distal end 14 of shaft 12 and includes opposing jaw members 110, 120 pivotably coupled to one another. Each of the jaw members 110 and 120 includes a jaw body 111, 121 supporting the respective electrically-conductive surface 112, 122, and a respective proximally-extending jaw flange 114, 124. Flanges 114, 124 are pivotably coupled to one another to permit movement of jaw members 110, 120 relative to one another between a spaced-apart position (FIG. 2A) and an approximated position (FIG. 2B) for grasping tissue between surfaces 112, 122. One or both of surfaces 112, 122 are adapted to connect to a source of energy (not explicitly shown), e.g., via the wires (not shown) of cable 2 (FIG. 1) and are configured to conduct energy through tissue grasped therebetween to treat, e.g., seal, tissue. More specifically, in some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating e.g., sealing, tissue. Activation switch 4 (FIG. 1) is operably coupled between the source of energy (not shown) and surfaces 112, 122, thus allowing the user to selectively apply energy to surfaces 112, 122 of jaw members 110, 120, respectively, of end effector assembly 100 during a bipolar mode of operation.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife channel 115, 125 (FIGS. 4A-4B) may be defined within one or both of jaw members 110, 120 to permit reciprocation of a knife 184 (FIGS. 4A-4B) therethrough, e.g., upon actuation of a trigger 62 of trigger assembly 60, to cut tissue grasped between jaw members 110, 120.

Figure 2D:
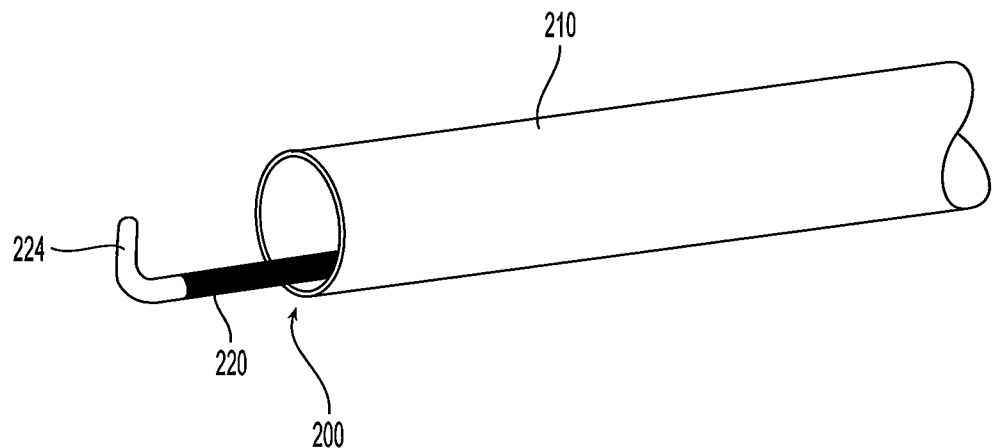
FIG. 2D is an enlarged, front, perspective view of the end effector assembly of FIG. 2A, wherein the monopolar assembly is disposed in the deployed position.
Figure 3:
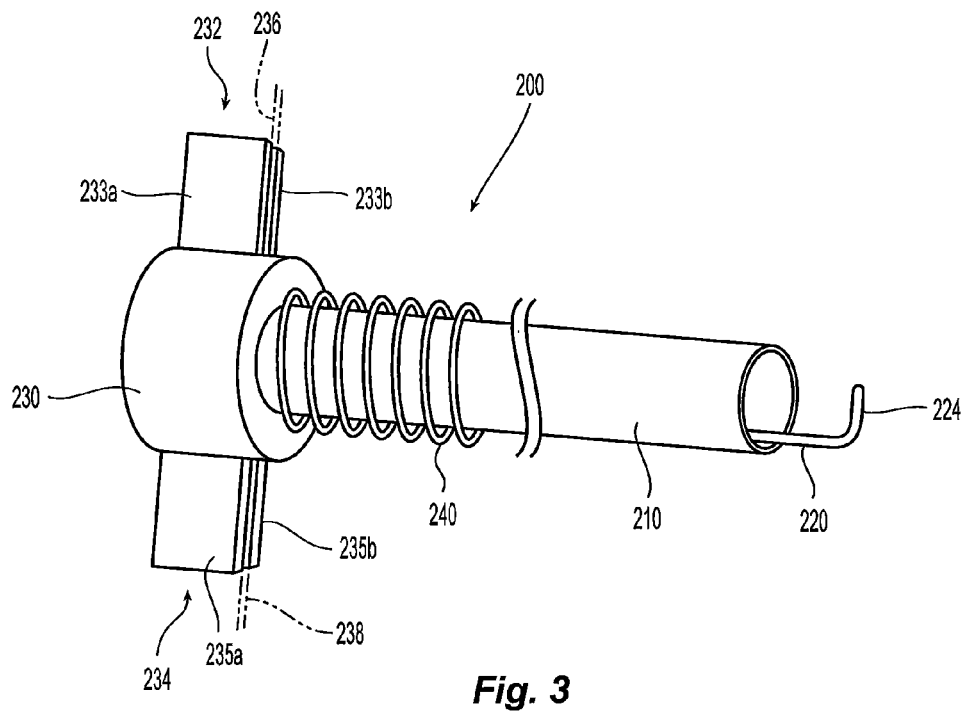
FIG. 3 is a perspective view of the monopolar assembly of the forceps of FIG. 1.

Referring to FIGS. 1-3, monopolar assembly 200 includes an insulative sleeve 210, an energizable rod member 220, a proximal hub 230, and a biasing member 240. Insulative sleeve 210 is slidably disposed about shaft 12 and is selectively movable about and relative to shaft 12 and end effector assembly 100 between a storage position (FIG. 2B), wherein insulative sleeve 210 is disposed proximally of end effector assembly 100, and a deployed position (FIG. 2D), wherein insulative sleeve 210 is substantially disposed about end effector 100 so as to electrically insulate surfaces 112, 122 of jaw members 110, 120, respectively, from the surroundings of insulative sleeve 210. As shown in FIG. 3, proximal hub 230 is rotatably coupled to insulative sleeve 210 at the proximal end of insulative sleeve 210. Proximal hub 230 includes a pair of opposed flanges 232, 234 extending radially outwardly from proximal hub 230. Each flange 232, 234 includes a pair of spaced-apart flange components 233a, 233b and 235a, 235b, respectively, that define respective elongated gaps 236, 238 therebetween. Biasing member 240 is positioned about insulative sleeve 210 distally of hub 230, although other suitable biasing members and/or biasing configurations are also contemplated. The distal end of biasing member 240 is configured to contact an interior portion (not explicitly shown) of housing 20 and compress upon advancement of insulative sleeve 210, thus biasing insulative sleeve 210 towards the storage position (FIG. 2B).

Continuing with reference to FIGS. 1-3, energizable rod member 220 extends through sleeve 210 and distally therefrom, ultimately defining an electrically-conductive distal tip 224. Energizable rod member 220 and, more specifically, distal tip 224 thereof, functions as the active electrode of monopolar assembly 200. The one or more wires (not shown) extending from cable 2 through housing 20 (see FIG. 1), are coupled to energizable rod member 220 to provide energy to energizable rod member 220, e.g., upon actuation of activation switch 4 (FIG. 1) in a monopolar mode, for treating tissue in a monopolar mode of operation. Energizable rod member 220 is movable between a storage position (FIG. 2B), wherein distal tip 224 of rod member 220 is positioned adjacent proximal flange 124 of jaw member 120, and a deployed position (FIG. 2D), wherein distal tip 224 of rod member 220 extends distally from the distal ends of jaw members 110, 120. Distal tip 224 may be hook-shaped (as shown), or may define any other suitable configuration, e.g., linear, circular, angled, etc.

Sleeve 210 and rod member 220 are coupled to one another and sleeve 210 is engaged to hub 230 such that sleeve 210 and rod member 220 move in concert with one another between their storage positions (FIG. 2B), e.g., the storage condition of monopolar assembly 200, and their deployed positions (FIG. 2D), e.g., the deployed condition of monopolar assembly 200, upon selective translation of hub 230, as will be detailed below. In the storage position, as shown in FIGS. 2A-2B, distal tip 224 of rod member 220 of monopolar assembly 200 is disposed within an insulated groove 126 defined within proximal flange 124 of jaw member 120, although other configurations are also contemplated. Insulated groove 126 electrically-insulates distal tip 224 of rod member 220 from electrically-conductive surfaces 112, 122 of jaw members 110, 120, respectively, and from surrounding tissue when disposed in the storage position. Alternatively, distal tip 224 of rod member 220 may only be insulated from surface 112. In such configurations, distal tip 224 of rod member 220 is capable of being energized to the same polarity as surface 122. In the extended position, as shown in FIG. 2D, distal tip 224 of rod member 220 extends distally from end effector assembly 100 and insulative sleeve 210, which substantially surrounds end effector assembly 100. In this position, energy may be applied to distal tip 224 of rod member 220 to treat tissue, e.g., via activation of activation switch 4 (FIG. 1) in the monopolar mode.

With reference again to FIG. 1, handle assembly 30 includes a movable handle 40 and a fixed handle 50. Fixed handle 50 is integrally associated with housing 20 and movable handle 40 is movable relative to fixed handle 50. Movable handle 40 is movable relative to fixed handle 50 between an initial position, wherein movable handle 40 is spaced from fixed handle 50, and a compressed position, wherein movable handle 40 is compressed towards fixed handle 50. A biasing member (not shown) may be provided to bias movable handle 40 towards the initial position. Movable handle 40 is ultimately connected to a drive assembly (not shown) that, together, mechanically cooperate to impart movement of jaw members 110, 120 between the spaced-apart position (FIG. 2A), corresponding to the initial position of movable handle 40, and the approximated position (FIG. 2B), corresponding to the compressed position of movable handle 40. Any suitable drive assembly for this purpose may be provided.

Referring to FIGS. 1 and 4A-5, trigger assembly 60 includes trigger 62 that is operably coupled to a knife assembly 180. Knife assembly 180 includes a knife drive bar 182 having a knife 184 extending from the distal end thereof and a knife hub 186 disposed at the proximal end thereof. A knife biasing member 188 is disposed about knife drive bar 182 distally of knife hub 186 to bias knife assembly 180 proximally in a similar fashion as biasing member 240 of monopolar assembly 200 (FIG. 3). Trigger 62 of trigger assembly 60 is selectively actuatable from an un-actuated position to an actuated position to advance knife 184 from a retracted position (FIG. 4A), wherein knife 184 is disposed proximally of jaw members 110, 120, to an extended position (FIG. 4B), wherein knife 184 extends at least partially between jaw members 110, 120 and through knife channels 115, 125 (FIGS. 4A-4B), respectively, to cut tissue grasped between jaw members 110, 120. Trigger assembly 60 is described in greater detail below.

Figure 5:
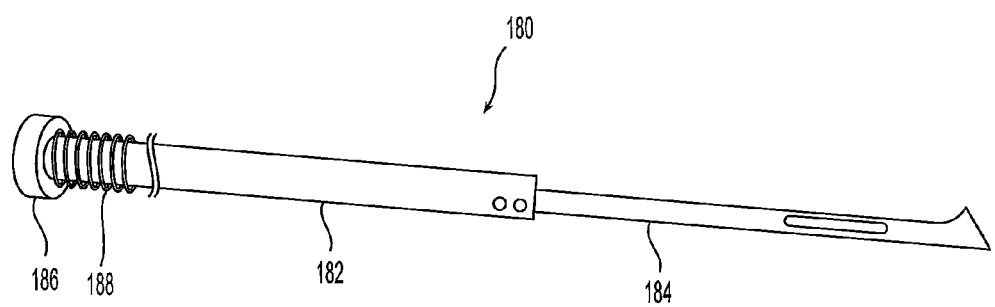
FIG. 5 is a perspective view of the knife assembly of the forceps of FIG. 1.
Figure 4A:
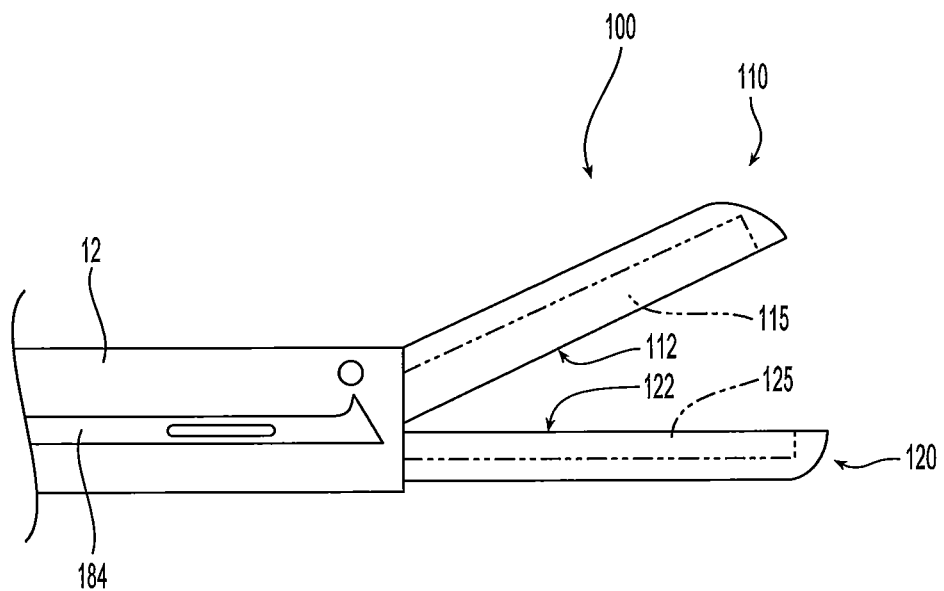
FIG. 4A is a longitudinal, cross-sectional view of the end effector assembly of FIG. 2A with the jaw members disposed in the spaced-apart position and wherein a knife is disposed in a retracted position.
Figure 6:
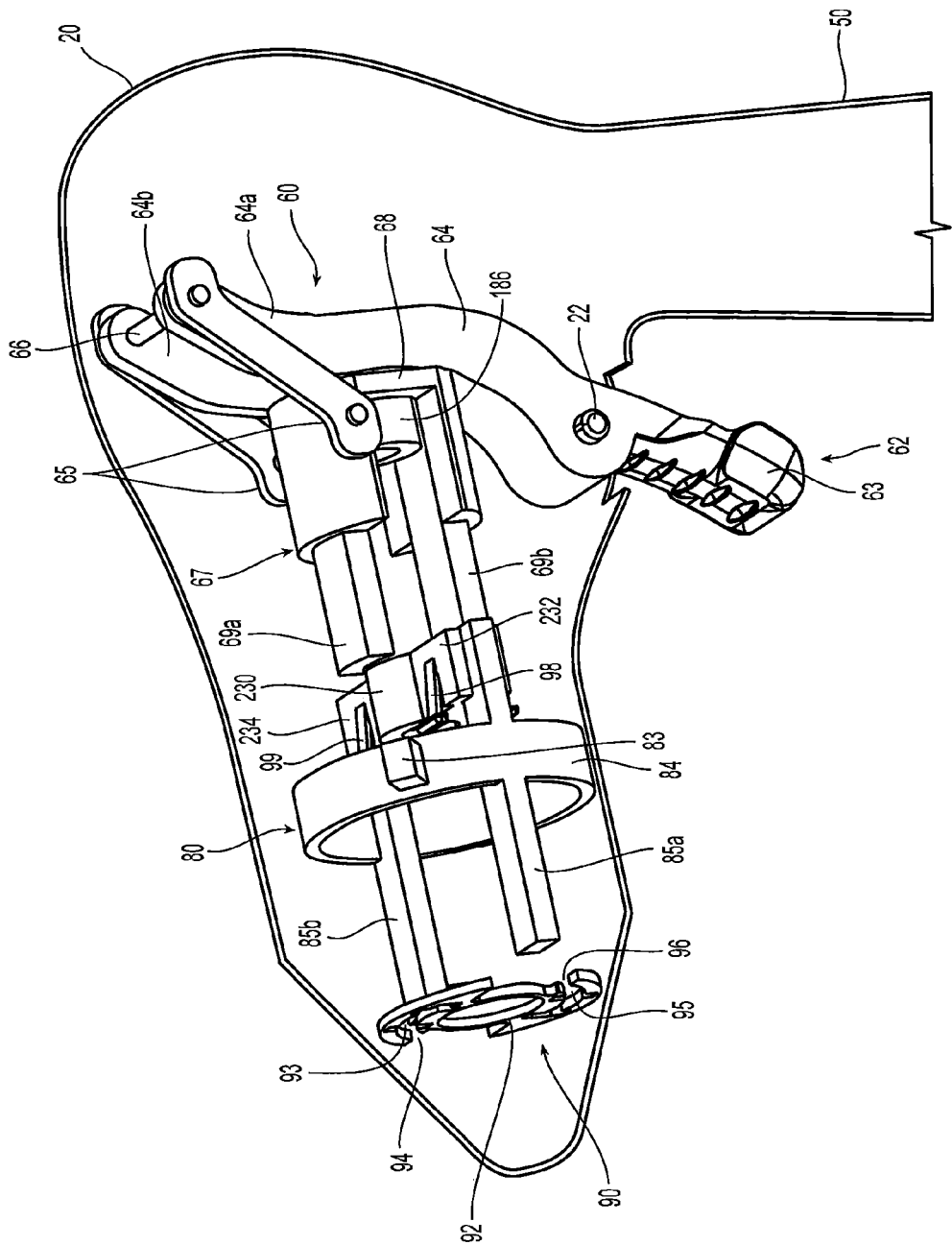
FIG. 6 is a perspective, cut-a-way view of the housing of the forceps of FIG. 1 including a selector assembly and a trigger assembly, wherein the selector assembly is disposed in a first state and the trigger assembly is disposed in an un-actuated state.
Figure 7:
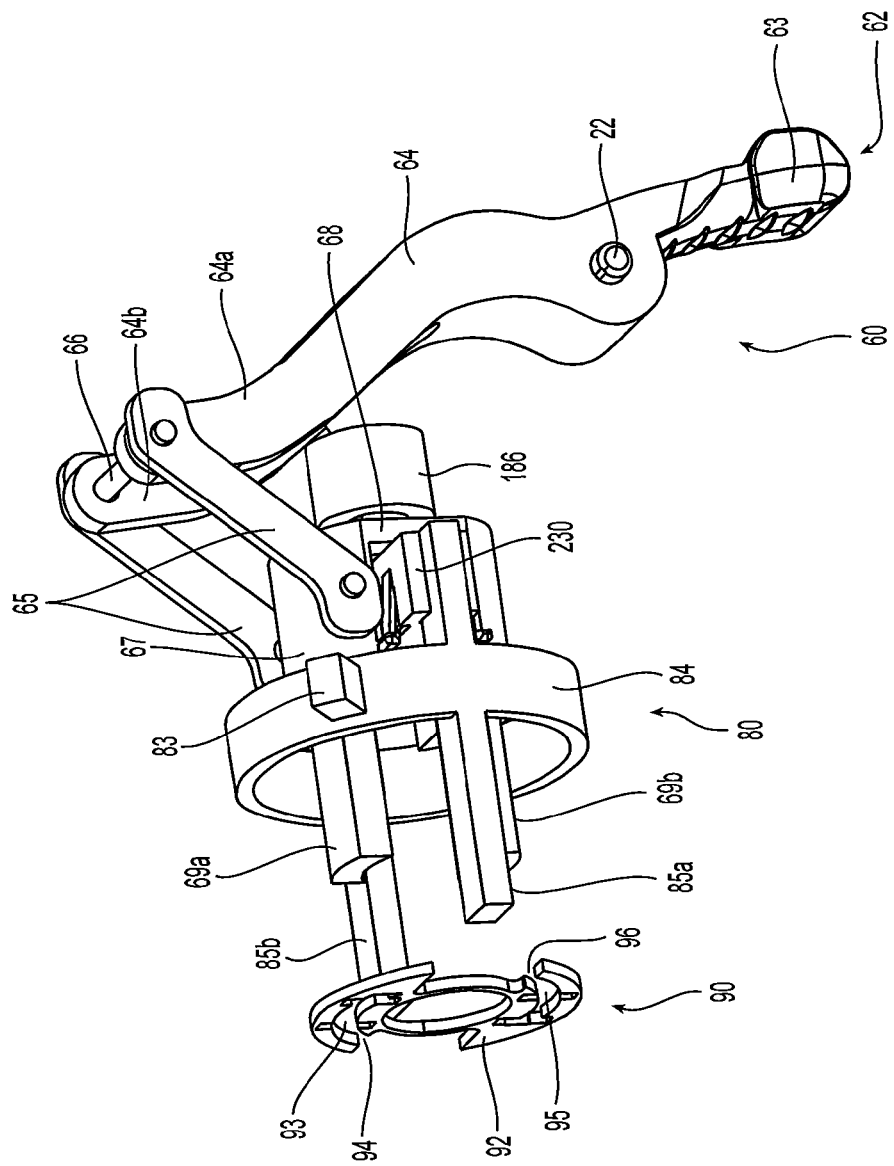
FIG. 7 is a perspective view of the selector assembly and trigger assembly of FIG. 6 wherein the selector assembly is disposed in the first state and the trigger assembly is disposed in the actuated state.
Figure 8:
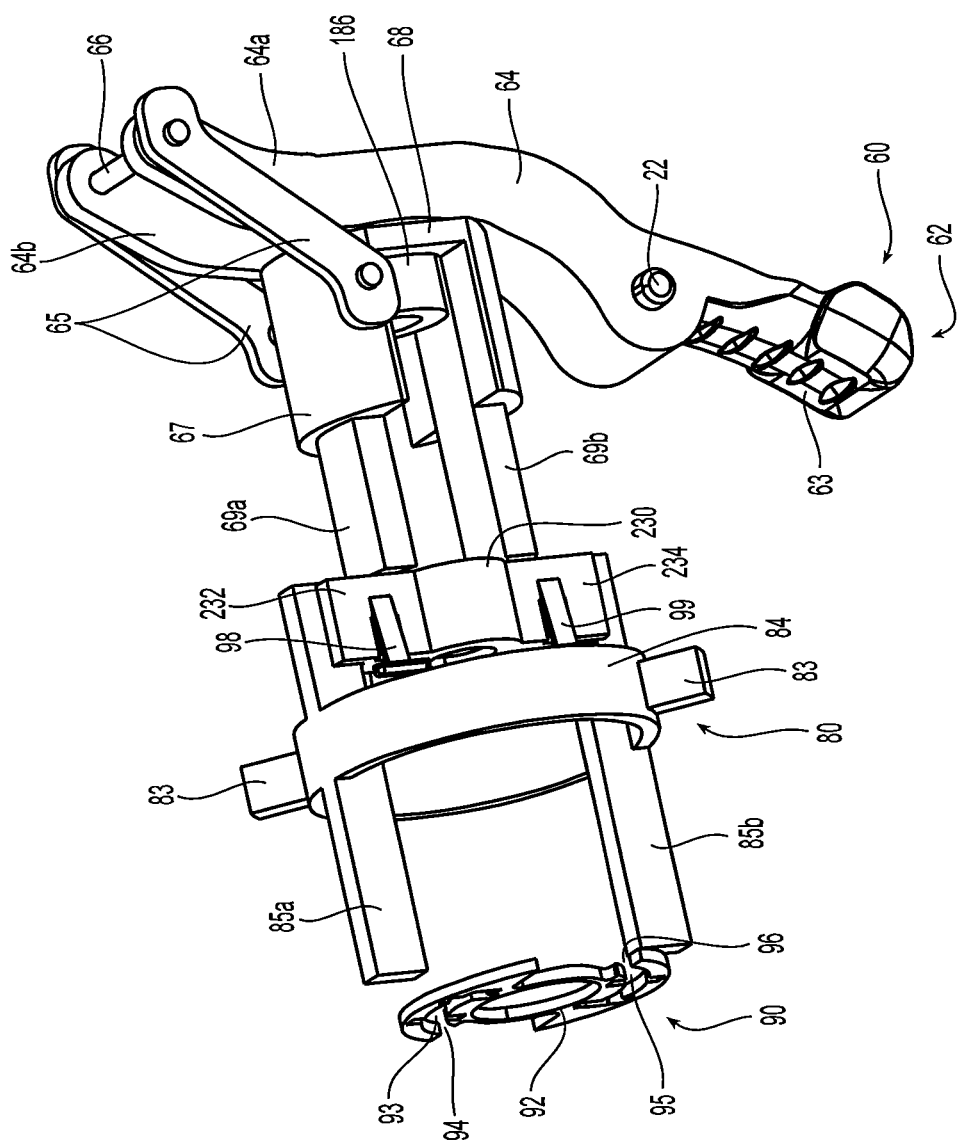
FIG. 8 is a perspective view of the selector assembly and trigger assembly of FIG. 6 wherein the selector assembly is disposed in a second state and the trigger assembly is disposed in the un-actuated state.
Figure 9:
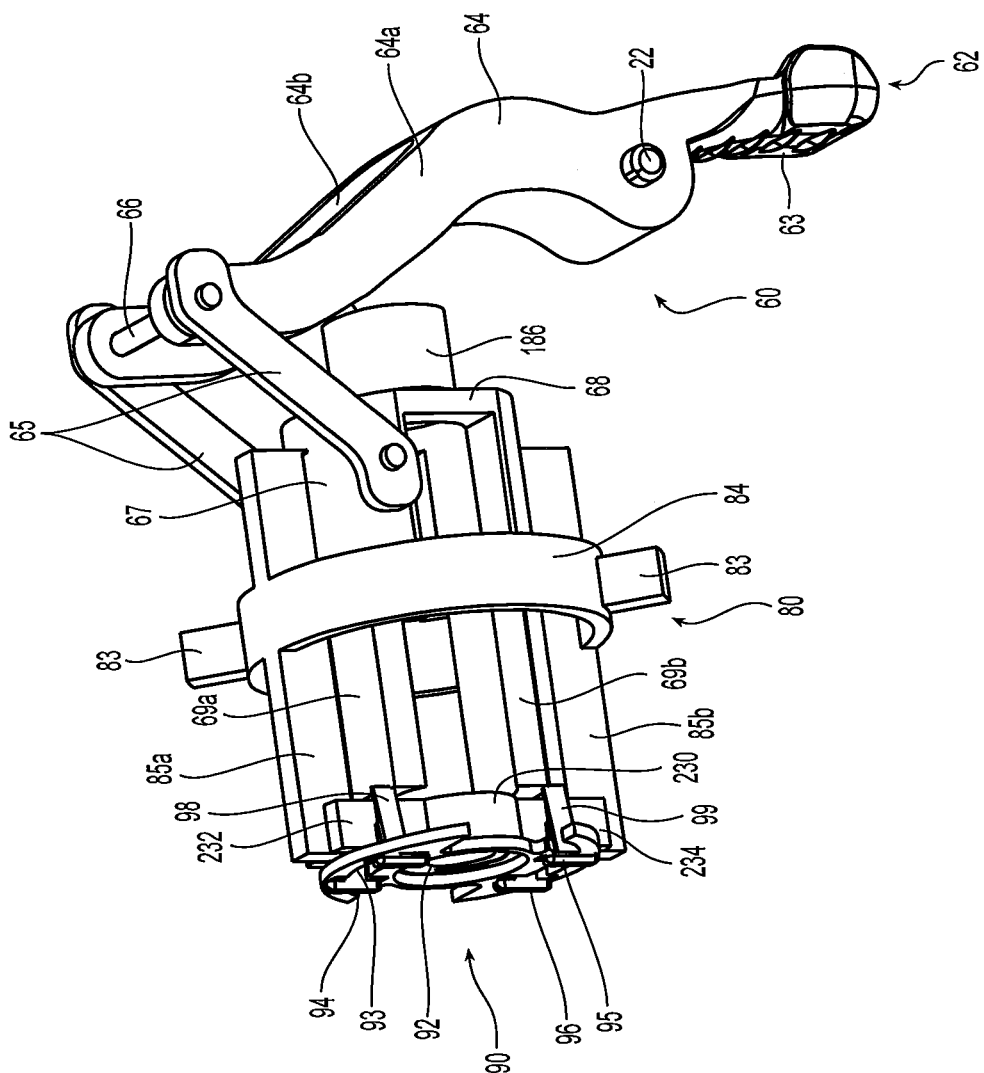
FIG. 9 is a perspective view of the selector assembly and trigger assembly of FIG. 6 wherein the selector assembly is disposed in the second state and the trigger assembly is disposed in the actuated state.

With additional reference to FIGS. 6-9, trigger assembly 60 includes trigger 62, a linkage 65, and a slider 67. Trigger 62 includes a toggle member 63 and a bifurcated arm 64 extending from toggle member 63 and into housing 20. Trigger 62 is pivotably coupled to housing 20 via pivot pin 22, which extends through an intermediate portion of trigger 62, e.g., between toggle member 63 and bifurcated arm 64. As such, trigger 62 is capable of being pivoted about pivot pin 22 and relative to housing 20 between the un-actuated position (FIGS. 6 and 8) and the actuated position (FIGS. 7 and 9). Upon pivoting of trigger 62 from the un-actuated position (FIGS. 6 and 8) towards the actuated position (FIGS. 7 and 9), arm 64 contacts knife hub 186 of knife assembly 180 and urges knife hub 186 distally to thereby translate knife 184 (FIG. 5) from the retracted position (FIG. 4A) towards the extended position (FIG. 4B) against the bias of knife biasing member 188 (FIG. 5). Upon release or return of trigger 62, knife hub 186 is returned under the bias of knife biasing member 188 (FIG. 5), thereby returning knife 184 (FIG. 5) to the retracted position (FIG. 4A). Only knife hub 186 of knife assembly 180 (FIG. 5) is shown in FIGS. 6-9 while the other components of knife assembly 180 (FIG. 5) are not shown to avoid obscuring the details of trigger assembly 60 and selector assembly 80.

Arm 64 of trigger 62 is bifurcated to define first and second spaced-apart flanges 64a, 64b to permit passage of arm 64 about the drive assembly (not shown) associated with handle assembly 30 and jaw members 110, 120 (FIG. 1) for moving jaw members 110, 120 between the spaced-apart position (FIG. 2A) and the approximated position (FIG. 2B). A pin 66 pivotably couples the free ends of flanges 64a, 64b of trigger 62 to a proximal end of linkage 65. Linkage 65, in turn, is pivotably coupled to slider 67 at a distal end of linkage 65. As such, upon pivoting of trigger 62 from the un-actuated position (FIGS. 6 and 8) towards the actuated position (FIGS. 7 and 9), linkage 65 and slider 67 are translated distally. Upon return of trigger 62 towards the un-actuated position (FIGS. 6 and 8), slider 67 is returned proximally. Slider 67 includes a proximal base 68 defining an aperture (not explicitly shown) configured permit knife hub 186 to pass therethrough, and first and second spaced-apart arms 69a, 69b extending distally from proximal base 68. As will be detailed below, arms 69a, 69b are configured such that, in a first state of selector assembly 80, actuation of trigger 62 translates arms 69a, 69b distally about proximal hub 230 of monopolar assembly 200 (FIG. 3) while proximal hub 230 remains stationary. However, in a second state of selector assembly 80, actuation of trigger 62 translates arms 69a, 69b distally into contact with proximal hub 230 to urge proximal hub 230 and, thus, monopolar assembly 200 (FIG. 3) to translate distally. Selector assembly 80 and the first and second states thereof will be detailed below.

Referring to FIGS. 1 and 6-9, selector assembly 80 includes a selector member 82 (FIG. 1) disposed on either or both sides of housing 20 (only one selector member 82 is shown). Selector member 82 extends through an arcuate slot 24 defined within housing 20 and is movable along slot 24 between first and second ends 24a, 24b, respectively, thereof to transition selector assembly 80 between the first state (FIGS. 6, 7, and 10A), corresponding to the bipolar mode of operation of forceps 10, and the second state (FIGS. 8, 9, and 10B), corresponding to the monopolar mode of operation of forceps 10. As a result of the configuration of arcuate slot 24 of housing 20, as selector member 82 is moved along slot 24 between first and second ends 24a, 24b, respectively, selector member 82 is moved along an arc defining a radius of curvature.

Selector assembly 80 further includes a selector ring 84 rotatably coupled to housing 20. Selector ring 84 includes first and second longitudinally-extending bars 85a, 85b coupled to selector ring 84 at radially-opposed positions. A portion of each bar 85a, 85b extends distally from selector ring 84, while another portion of each bar 85a, 85b extends proximally from selector ring 84. Bars 85a, 85b are configured to be slidably received within elongated gaps 236, 238 defined between the flange components 233a, 233b and 235a, 235b of each flange 232, 234, respectively, of proximal hub 230 of monopolar assembly 200 (FIG. 3) such that flanges 232, 234 may be translated along bars 85a, 85b to permit actuation of monopolar assembly 200 (FIG. 3) and such that flanges 232, 234 are rotatably fixed relative to selector ring 84, e.g., such that rotation of selector ring 84 effects similar rotation of flanges 232, 234 and proximal hub 230. Selector ring 84 further includes one or more engagement posts 83 disposed on the outer periphery thereof and extending radially outwardly therefrom. Each engagement post 83 engages one of the selector members 82 such that movement of any one of selector members 82 along its corresponding slot 24 effects rotation of selector ring 84 and, thus, proximal hub 230 to transition selector assembly 80 between the first state (FIGS. 6, 7, and 10A) and the second state (FIGS. 8, 9, and 10B). Only proximal hub 230 of monopolar assembly 200 (FIG. 3) is shown in FIGS. 6-9 while the other components of monopolar assembly 200 (FIG. 3) are not shown to avoid obscuring the details of trigger assembly 60 and selector assembly 80.

Figure 10A:
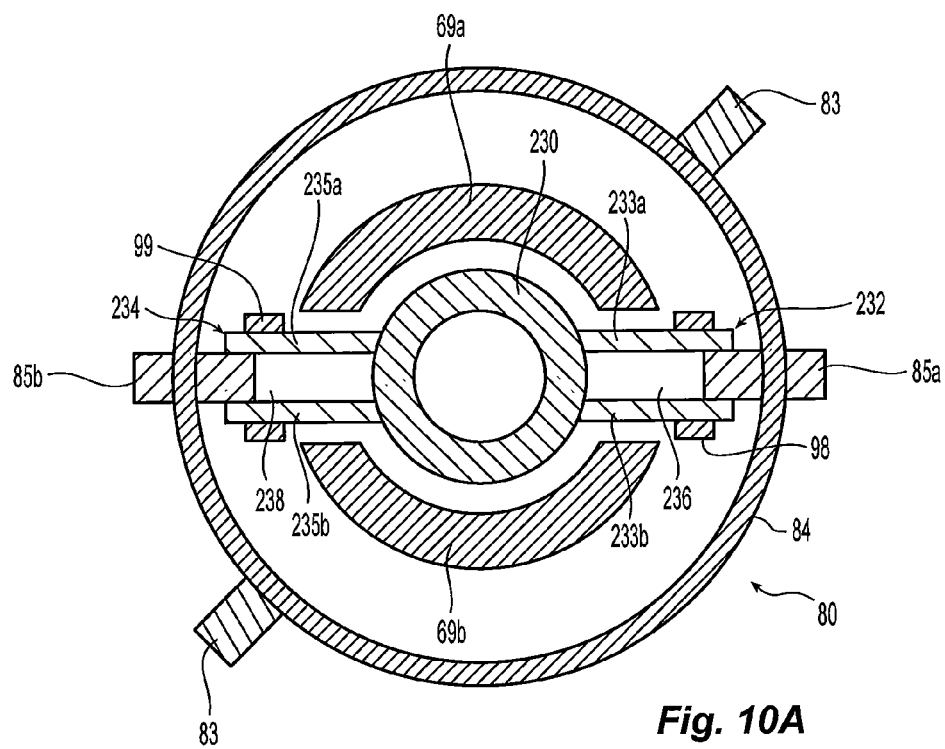
FIG. 10A is a transverse, cross-sectional view of the selector assembly of FIG. 6, disposed in the first state.
Figure 10B:
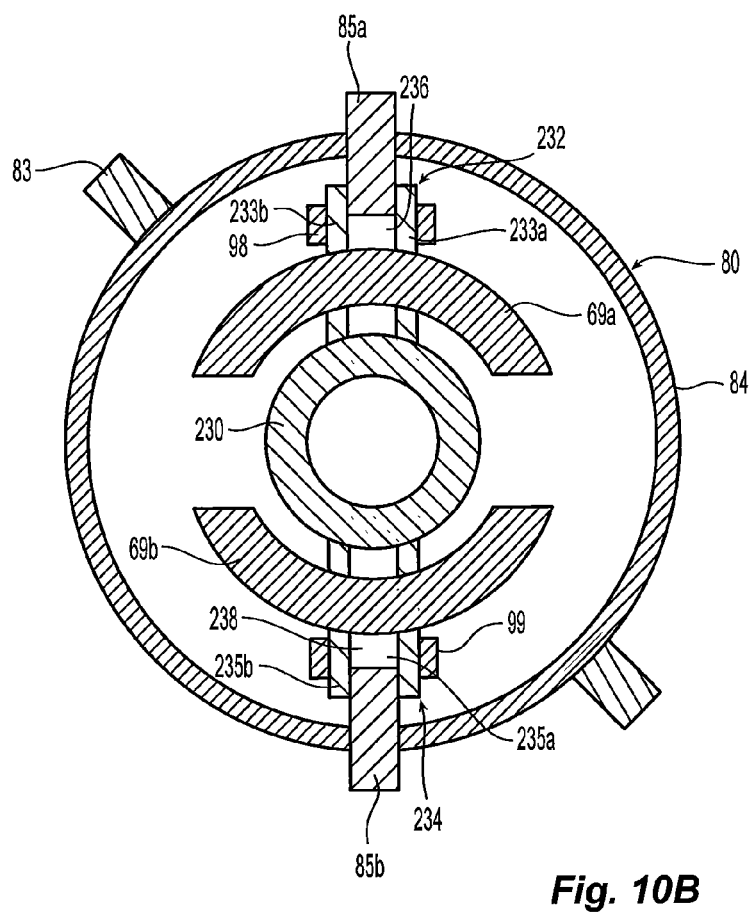
FIG. 10B is a transverse, cross-sectional view of the selector assembly of FIG. 6, disposed in the second state.

Referring momentarily to FIG. 10A, in the first state of selector assembly 80, selector ring 84 and flanges 232, 234 of proximal hub 230 of monopolar assembly 200 (FIG. 3) are disposed in a first orientation, wherein flanges 232, 234 are displaced from the travel path of arms 69a, 69b of slider 67. As such, with selector assembly 80 disposed in the first state, actuation of trigger 62 translates arms 69a, 69b distally about proximal hub 230 without contacting proximal hub 230. Thus, only knife assembly 180 (FIG. 5) is capable of being actuated in the first state of selector assembly 80, while monopolar assembly 200 (FIG. 3) remains disposed in the storage condition (FIGS. 2A and 2B).

Referring momentarily to FIG. 10B, in the second state of selector assembly 80, selector ring 84 and flanges 232, 234 of proximal hub 230 of monopolar assembly (FIG. 3) are disposed in a second orientation, wherein flanges 232, 234 intersect the travel path of arms 69a, 69b of slider 67. As such, with selector assembly 80 disposed in the second state, actuation of trigger 62 translates arms 69a, 69b distally into contact with flanges 232, 234, respectively, of proximal hub 230 to urge proximal hub 230 and, thus, monopolar assembly 200 (FIG. 3) distally. Thus, both knife assembly 180 (FIG. 5) and monopolar assembly 200 are actuatable, in conjunction with one another, in the second state of selector assembly 80.

With reference again to FIGS. 6-9, selector assembly 80 may further include a lock mechanism 90 operably associated therewith for selectively locking monopolar assembly 200 (FIG. 3) in the deployed position (FIG. 2D). As monopolar assembly 200 (FIG. 3) is only actuatable in the second state of selector assembly 80, lock mechanism 90 is likewise only operable in the second state of selector assembly 80.

Lock mechanism 90 includes a locking plate 92 and first and second latch members 98, 99. Locking plate 92 defines first and second tracks 93, 95 each having an opening 94, 96 and is fixedly retained within housing 20. Latch members 98, 99 are disposed on flanges 232, 234, respectively, of proximal hub 230 of monopolar assembly 200 (FIG. 3) and are configured for one-way movement. That is, latch members 98, 99 are capable of being flexed to permit passage into tracks 93, 95 when translating in a proximal to distal direction, but inhibit flexing and, thus, removal from tracks 93, 95 when urged in a distal to proximal direction. Accordingly, upon actuation of trigger assembly 60 to actuate monopolar assembly 200 (FIG. 3), arms 69a, 69b urge flanges 232, 234, respectively, distally such that latch members 98, 99 are urged to flex and pass through tracks 93, 95, respectively. Once this position has been achieved, as a result of the one-way configuration of latch members 98, 99, return of monopolar assembly 200 (FIG. 3) proximally is inhibited. Thus, even upon release of trigger 62, monopolar assembly 200 (FIG. 3) is locked in the deployed condition. In order to release monopolar assembly 200 (FIG. 3) to permit monopolar assembly 200 (FIG. 3) to return to the storage condition, selector assembly 80 is transitioned from the second state back to the first state, e.g., via movement of one of selector members 82 (FIG. 1). The transition of selector assembly 80 from the second state back to the first state rotates selector ring 84 and flanges 232, 234 relative to locking plate 92 such that latch members 98, 99 are rotated into alignment with openings 94, 96 of tracks 93, 95. Once aligned or oriented with openings 94, 96, latch members 98, 99 are permitted to exit tracks 93, 95, thus allowing monopolar assembly 200 (FIG. 3) to return under bias to the storage condition.

Referring to FIGS. 1-10B, the use and operation of forceps 10 in both the bipolar mode, e.g., for grasping, treating and/or cutting tissue, and the monopolar mode, e.g., for electrical/electromechanical tissue treatment, is described.

Initially, with respect to the bipolar mode, selector member 82 is moved along slot 24 defined within housing 20 to orient selector assembly 80 in the first state, shown in FIGS. 6, 8, and 10A, wherein only knife assembly 180 (FIG. 5) is capable of being actuated. That is, in the first state of selector assembly 80, monopolar assembly 200 remains disposed in the storage condition (FIGS. 2A and 2B).

Referring now to FIGS. 1 and 2A, jaw members 110, 120 are shown disposed in the spaced-apart position and monopolar assembly 200 is shown disposed in the storage condition wherein insulative sleeve 210 is positioned proximally of jaw members 110, 120 and energizable rod member 220 is disposed in the retracted position within insulative groove 126 of jaw flange 124 of jaw member 120. At this point, trigger assembly 60 is disposed in the un-actuated position such that knife 184 (FIG. 5) is disposed in the retracted position (FIG. 4A).

With jaw members 110, 120 disposed in the spaced-apart position (FIG. 2A), end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween, as shown in FIG. 2B. In this approximated position, energy may be supplied, e.g., via activation of switch 4, to plate 112 of jaw member 110 and/or plate 122 of jaw member 120 and conducted through tissue to treat tissue, e.g., to effect a tissue seal or otherwise treat tissue in the bipolar mode of operation.

Figure 4B:
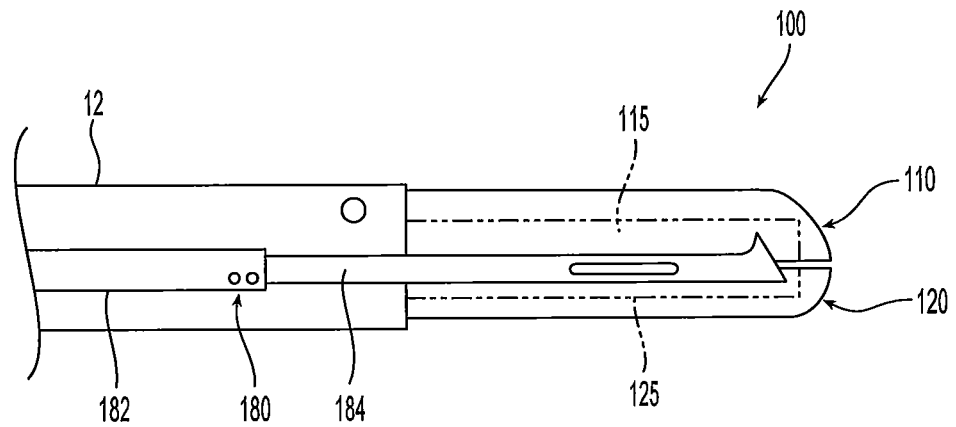
FIG. 4B is a longitudinal, cross-sectional view of the end effector assembly of FIG. 2A with the jaw members disposed in the approximated position and wherein the knife is disposed in an extended position.

With additional reference to FIGS. 4A, 4B, 6, 7, and 10A, once tissue treatment is complete (or to cut untreated tissue), knife 184 of knife assembly 180 may be deployed from within shaft 12 to between jaw members 110, 120, e.g., via actuation of trigger 62 of trigger assembly 60 (see FIG. 1), to cut tissue grasped therebetween. More specifically, upon actuation of trigger 62, from the un-actuated position (FIG. 6) towards the actuated position (FIG. 7), trigger 62 is pivoted such that arm 64 is urged into contact with knife hub 186 to likewise urge knife hub 186 distally. The distal urging of knife hub 186 urges knife 184 to translate distally from the retracted position (FIG. 4A) towards the extended position (FIG. 4B) to extend at least partially through knife channels 115, 125 of jaw members 110, 120, respectively, to cut tissue grasped between jaw members 110, 120 (FIG. 4B). Although slider 67 is also translated distally upon actuation of trigger 62, monopolar assembly 200 remains disposed in the storage condition (FIG. 2B) because, with selector assembly 80 disposed in the first state, arms 69a, 69b of slider 67 pass distally about proximal hub 230 of monopolar assembly 200 without contacting proximal hub 230.

When tissue cutting is complete, trigger 62 may be released to allow knife 184 to return under bias to the retracted position. Thereafter, jaw members 110, 120 may be moved back to the spaced-apart position (FIG. 2A) to release the treated and/or divided tissue.

Referring to FIGS. 1-3, 8, 9, and 10B, for operation of forceps 10 in the monopolar mode, selector member 82 is moved along slot 24 defined within housing 20 to orient selector assembly 80 in the second state, shown in FIGS. 8, 9, and 10B, wherein flanges 232, 234 intersect the travel path of arms 69a, 69b of slider 67 such that actuation of trigger 62 actuates both knife assembly 180 (FIG. 5) and monopolar assembly 200 in conjunction with one another.

With selector assembly 80 disposed in the second state for monopolar operation, movable handle 40 is depressed relative to fixed handle 50 to pivot jaw member 110 relative to jaw member 120 from the spaced-apart position to the approximated position. With jaw members 110, 120 disposed in the approximated position, monopolar assembly 200 may be translated from the storage condition (FIG. 2B) to the deployed condition (FIG. 2D) via actuation of trigger assembly 60. More specifically, in order to translate insulative sleeve 210 and energizable rod member 220 of monopolar assembly 200 from their storage positions (FIG. 2B) to their deployed positions (FIG. 2D), trigger 62 is actuated from the position shown in FIG. 8 to the position shown in FIG. 9, whereby arms 69a, 69b are translated distally into contact with flanges 232, 234, respectively, of proximal hub 230 to urge proximal hub 230 and, thus, monopolar assembly 200 distally. Knife assembly 180 (FIG. 5) is also actuated via this actuation of trigger 62 to extend between jaw members 110, 120. In the deployed condition of monopolar assembly 200, as mentioned above, insulative sleeve 210 surrounds jaw members 110, 120 (FIG. 2D) and energizable rod member 220 extends distally from end effector assembly 100 and insulative sleeve 210 (FIG. 2D).

Upon full actuation of trigger 62, e.g., upon monopolar assembly 200 reaching the deployed condition (FIG. 2D), latch members 98, 99 are urged to flex and pass through tracks 93, 95, respectively, of locking plate 92. As such, once the deployed position has been achieved, monopolar assembly 200 is locked in the deployed condition. With monopolar assembly 200 locked in the deployed condition, activation switch 4 may be actuated to supply energy to energizable rod member 220 to treat, e.g., dissect, tissue. During application of energy to tissue via energizable rod member 220, forceps 10 may be moved relative to tissue, e.g., longitudinally, transversely, and/or radially, to facilitate electromechanical treatment of tissue. At the completion of tissue treatment, e.g., dissection, monopolar assembly 200 may be returned to the storage condition (FIG. 2B) via moving selector member 82 (FIG. 1) back to its initial position corresponding to the first state of selector assembly 80. The return of selector assembly 80 to the first state releases latch members 98, 99 from locking plate 92 and, thus, permits monopolar assembly 200 to return to the storage condition.

Turning now to FIGS. 11-14, another embodiment of a monopolar assembly and corresponding end effector assembly (only jaw member 1200 thereof is shown), trigger assembly 600, and selector assembly 800 configured for use with forceps 10 (FIG. 1) is shown. As detailed below, the monopolar assembly (FIGS. 12A and 12B) mainly differs from monopolar assembly 200 (FIG. 3) in that insulative sleeve 2100 and energizable rod member 2200 are configured to travel different distances between their respective storage and deployed positions. Only the differences between the embodiments will be detailed below, while similarities will be summarily described or omitted entirely for purposes of brevity.

Figure 11:
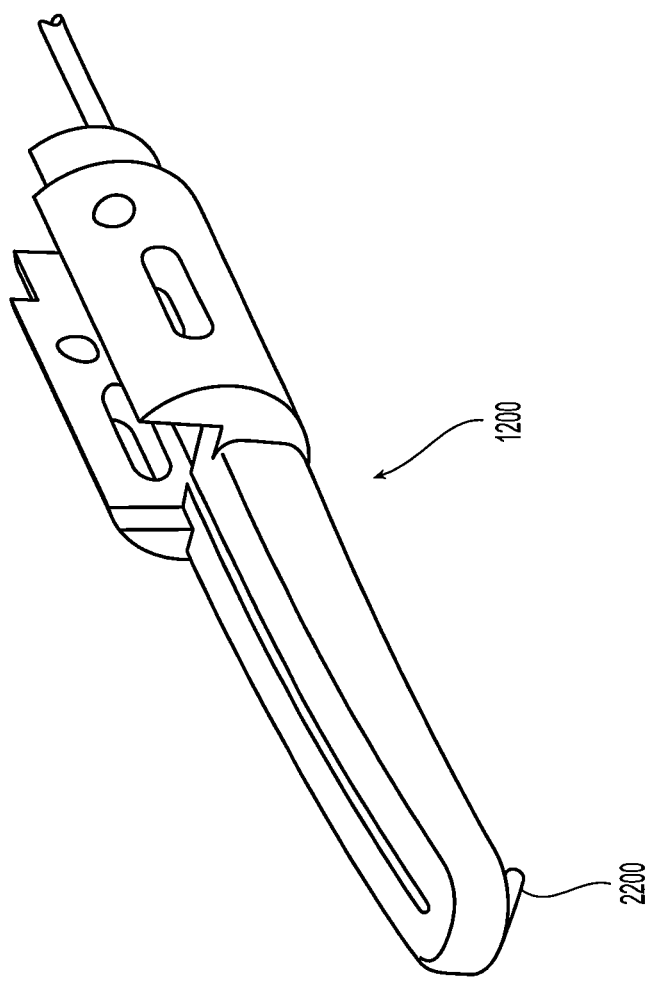
FIG. 11 is a perspective view of a jaw member of another embodiment of an end effector assembly configured for use with the forceps of FIG. 1.

Rather than being positioned alongside the proximal flange of jaw member 1200 as with energizable rod member 220 (FIG. 3), energizable rod member 2200 is stored on and extends along an underside of jaw member 1200, as best shown in FIG. 11. Jaw member 1200 may include an insulated groove (not shown, similar to insulated groove 126 (FIG. 2A)) or any other suitable structure for insulating and/or retaining energizable rod member 2200 when energizable rod member 2200 is disposed in the storage position. As a result of this above-noted positioning of energizable rod member 2200, insulative sleeve 2100 is required to travel further between its storage and deployed positions as compared to the length of travel of energizable rod member 2200 between its storage and deployed positions. Thus, energizable rod member 2200 and insulative sleeve 2100 cannot be fixed to one another. Instead, energizable rod member 2200 and insulative sleeve 2100 are separate components.

Figure 12A:
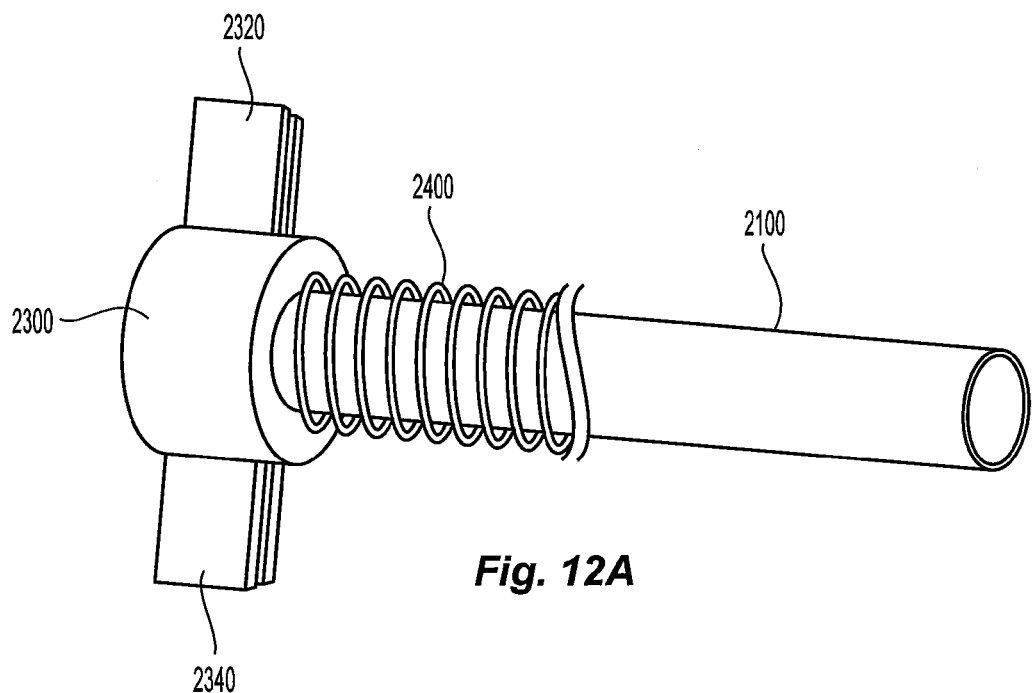
FIG. 12A is a perspective view of a first component of a monopolar assembly configured for use with the end effector assembly of FIG. 11.

Referring to FIG. 12A, insulative sleeve 2100 includes a proximal hub 2300 rotatably mounted at the proximal end thereof, and a biasing member 2400 disposed about insulative sleeve 2100 distally of proximal hub 2300. Proximal hub 2300 further includes flanges 2320, 2340 and functions similar to proximal hub 230 (FIG. 3) of monopolar assembly 200 (FIG. 3). That is, proximal hub 2300 is selectively movable when selector assembly 800 is disposed in the second state to move insulative sleeve 2100 between the storage position and the deployed position. Biasing member 2400, similarly as detailed above, is provided to bias insulative sleeve 2100 towards the storage position and is secured at its distal end within housing 20 of forceps 10 (see FIG. 1).

Figure 12B:
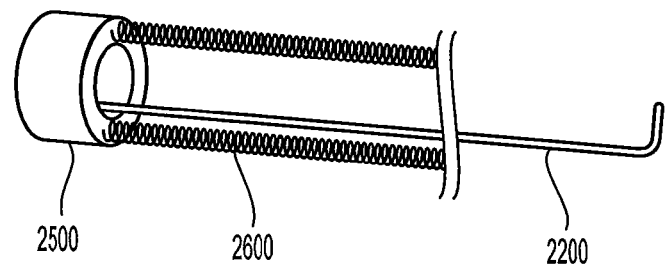
FIG. 12B is a perspective view of a second component of the monopolar assembly configured for use with the end effector assembly of FIG. 11.

With reference to FIG. 12B, energizable rod member 2200 includes a rod member hub 2500 mounted at the proximal end thereof and a pair of opposed rod member biasing members 2600. Rod member hub 2500 is positioned proximally of proximal hub 2300 and is inhibited from passing through proximal hub 2300 while rod member biasing members 2600 extend distally from rod member hub 2500 through proximal hub 2300. Energizable rod member 2200 extends distally through insulative sleeve 2100 (FIG. 12A). Insulative sleeve 2100 (FIG. 12A) may include slots or other suitable openings (not shown) to enable the distal ends of rod member biasing members 2600 to be secured relative to housing 20 of forceps 10 (see FIG. 1). Rod member biasing members 2600 are configured to bias rod member hub 2500 distally but together define a lower spring force than that of biasing member 2400.

Figure 13:
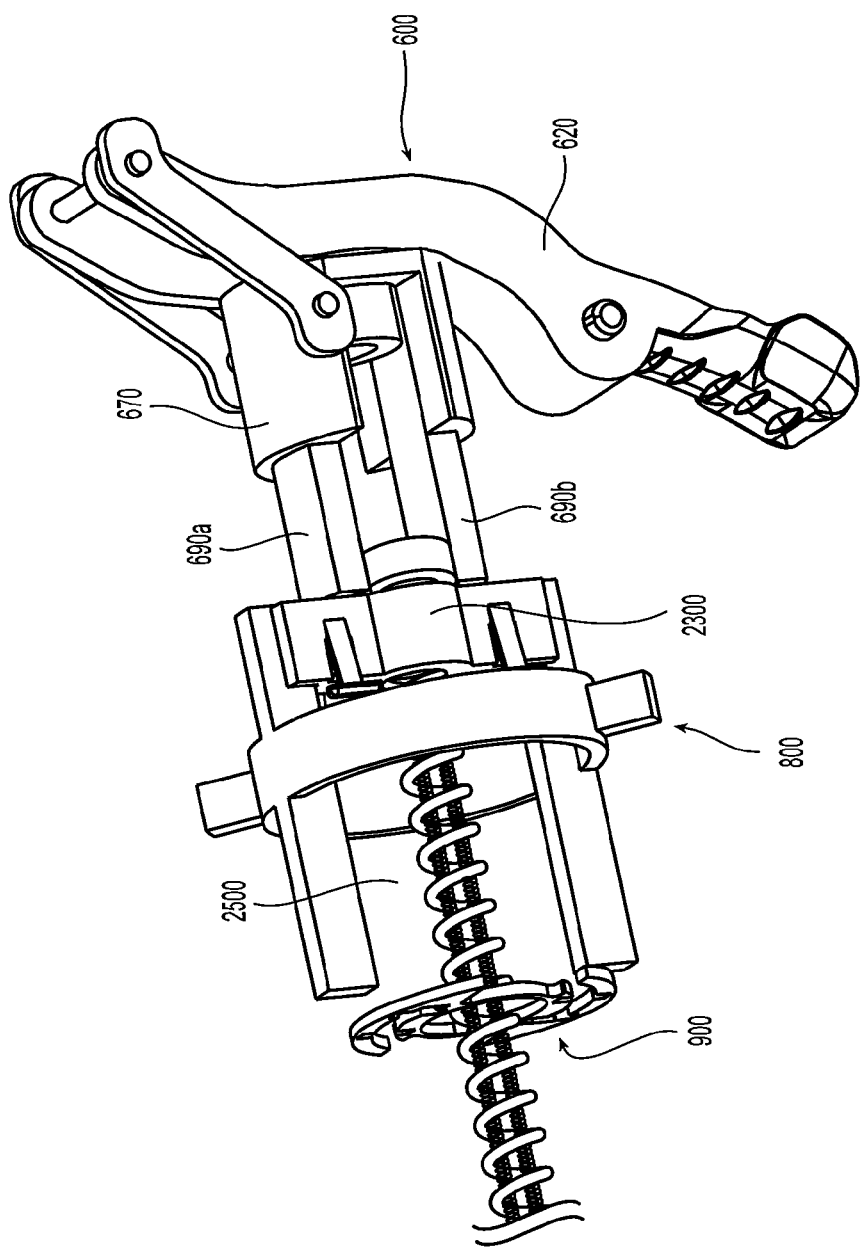
FIG. 13 a perspective view of a selector assembly and a trigger assembly configured for use with the end effector assembly of FIG. 11, with the selector assembly disposed in a second state and the trigger assembly disposed in an un-actuated state.
Figure 14:
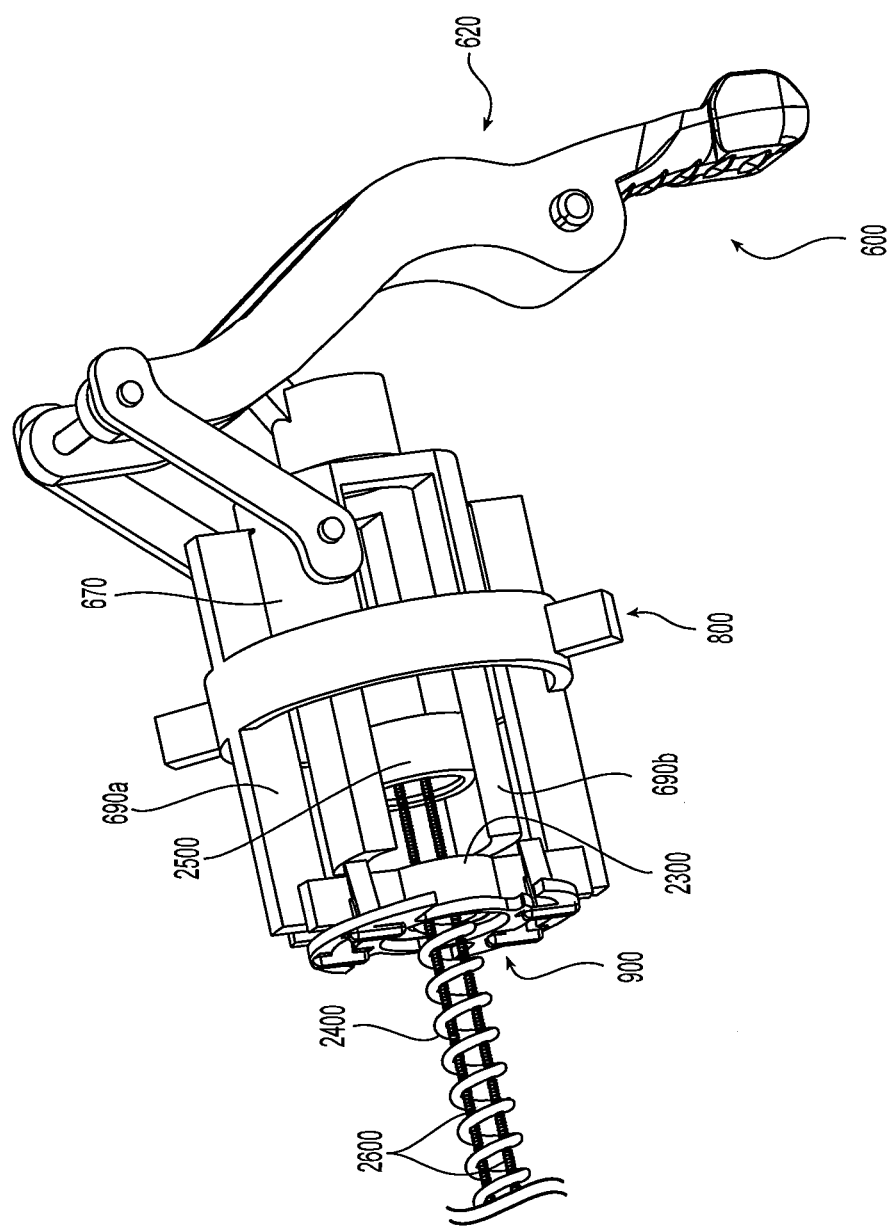
FIG. 14 is a perspective view of the selector assembly and trigger assembly of FIG. 13, wherein the selector assembly is disposed in the second state and the trigger assembly is disposed in the actuated state.

Referring to FIGS. 13 and 14, selector assembly 800 is shown disposed in the second state, wherein the monopolar assembly (FIGS. 12A and 12B) is selectively actuatable. Since the monopolar assembly (FIGS. 12A and 12B) is maintained in the storage condition in the first state of selector assembly 800, the use of the monopolar assembly (FIGS. 12A and 12B), trigger assembly 600, and selector assembly 800 in the bipolar mode of operation is similar to that detailed above with respect to the previous embodiments. Further, lock assembly 900 is configured and functions similarly as detailed above.

As shown in FIG. 13, in the second state of selector assembly 800, when trigger 620 of trigger assembly 600 is disposed in the un-actuated position, rod member hub 2500 is retained in abutment with proximal hub 2300 under the bias of rod member biasing members 2600, and biasing member 2400, having a larger spring force than that of rod member biasing members 2600, biases both proximal hub 2300 and rod member hub 2500 proximally to the respective storage conditions thereof. Referring additionally to FIG. 14, as trigger 620 is initially pivoted from the un-actuated position towards the actuated position, arms 690a, 690b of slider 670 of trigger assembly 600 urge proximal hub 2300 and, thus, insulative sleeve 2100 distally towards the deployed position. As proximal hub 2300 is urged distally, biasing member 2400 is compressed, allowing rod member hub 2500 to at least initially translate distally under the bias of rod member biasing members 2600, thereby translating energizable rod member 2200 towards its deployed position. Upon sufficient actuation of trigger 620 such that rod member biasing members 2600 reach their at-rest positions, rod member hub 2500 is disposed in its deployed position and is retained therein via rod member biasing members 2600, while proximal hub 2300 is permitted to continue translation to the deployed position thereof. As can be appreciated, in the respective deployed positions, rod member hub 2500 is proximally-spaced from proximal hub 2300 a distance equal to the difference between the travel lengths of energizable rod member 2200 and insulative sleeve 2100 such that, upon actuation, insulative sleeve 2100 and energizable rod member 2200 are together translated the deployment distance of energizable rod member 220, followed by insulative sleeve 2100 continuing to translate a distance equal to the difference between the deployment distances to the deployed position thereof. The features, use and operation are otherwise similar to that detailed above with respect to previous embodiments.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A surgical instrument, comprising:
an end effector assembly including first and second jaw members, at least one of the jaw members movable relative to the other between a spaced-apart position and an approximated position for grasping tissue therebetween;
a trigger assembly movable between an un-actuated position and an actuated position;
an energizable member selectively movable relative to the jaw members between a first storage position and a first deployed position, wherein at least a portion of the energizable member extends distally from the jaw members in the first deployed position;
a selector assembly operably associated with the trigger assembly and the energizable member, the selector assembly transitionable between a first state, wherein the energizable member is decoupled from the trigger assembly, and a second state, wherein the energizable member is coupled to the trigger assembly such that movement of the trigger assembly from the un-actuated position to the actuated position effects movement of the energizable member from the first storage position to the first deployed position; and
an insulative sleeve selectively movable relative to the jaw members between a second storage position, wherein the insulative sleeve is positioned proximally of the jaw members, and a second deployed position, wherein the insulative sleeve is disposed about the jaw members, wherein, in the first state of the selector assembly, the insulative sleeve is decoupled from the trigger assembly, and wherein, in the second state of the selector assembly, the insulative sleeve is coupled to the trigger assembly such that movement of the trigger assembly from the un-actuated position to the actuated position effects movement of the insulative sleeve from the second storage position to the second deployed position.

2. The surgical instrument according to claim 1, further comprising:
a knife selectively movable relative to the jaw members between a retracted position and an extended position, wherein the knife extends at least partially between the jaw members to cut tissue grasped therebetween,
wherein the knife is coupled to the trigger assembly such that movement of the trigger assembly from the un-actuated position to the actuated position moves the knife from the retracted position to the extended position in both the first and second states of the selector assembly.

3. The surgical instrument according to claim 1, further comprising an insulative groove defined within one of the jaw members, wherein the energizable member is disposed within the insulative groove in the first storage position and extends distally from the jaw members in the first deployed position.

4. The surgical instrument according to claim 1, wherein the energizable member and the insulative sleeve define equal travel lengths between their respective storage and deployed positions.

5. The surgical instrument according to claim 1, wherein the energizable member and the insulative sleeve define different travel lengths between their respective storage and deployed positions.

6. The surgical instrument according to claim 5, wherein the energizable member and the insulative sleeve move together between the respective storage positions thereof and the deployed position of the energizable member and wherein the insulative sleeve thereafter moves further to the deployed position of the insulative sleeve.

7. The surgical instrument according to claim 1, wherein the selector assembly includes a selector ring, the selector ring rotatable between a first orientation corresponding to the first state, and second orientation corresponding to the second state.

8. The surgical instrument according to claim 7, further comprising a hub associated with the energizable member and coupled to the selector ring, and a slider coupled to the trigger assembly, wherein the hub is displaced from a travel path of the slider in the first orientation of the selector ring, and wherein the hub intersects a travel path of the slider in the second orientation of the selector ring such that the slider is urged into contact with the hub upon actuation of the trigger assembly to move the energizable member from the first storage position to the first deployed position.

9. The surgical instrument according to claim 7, further comprising:
  a housing having a shaft extending distally from the housing, the end effector disposed at a distal end of the shaft; and
  a selector member disposed on the housing, the selector member coupled to the selector ring and movable between a first position and a second position relative to the housing to rotate the selector ring between the first orientation and the second orientation.

10. The surgical instrument according to claim 1, further comprising a lock assembly configured to lock the energizable member in the first deployed position upon movement of the energizable member to the first deployed position.

11. The surgical instrument according to claim 10, wherein the lock assembly is configured to unlock the energizable member from the deployed position in response to transitioning of the selector assembly from the second state back to the first state.

12. A surgical instrument, comprising:
  a housing;
  a shaft extending distally from the housing;
  an end effector assembly disposed at a distal end of the shaft, the end effector assembly including first and second jaw members, at least one of the jaw members movable relative to the other between a spaced-apart position and an approximated position for grasping tissue therebetween;
  a trigger assembly coupled to the housing, the trigger assembly including a trigger movable relative to the housing between an un-actuated position and an actuated position;
  a deployable assembly including an energizable member and an insulative sleeve, the deployable assembly selectively movable relative to the jaw members between a storage position and a deployed position;
  a selector assembly operably associated with the trigger assembly and the deployable assembly, the selector assembly including a selector member coupled to the housing, the selector member movable relative to the housing between a first position and a second position for transitioning the selector assembly between a first state, wherein the deployable assembly is decoupled from the trigger assembly, and a second state, wherein the deployable assembly is coupled to the trigger assembly such that movement of the trigger assembly from the un-actuated position to the actuated position effects movement of the deployable assembly from the storage position to the deployed position; and
  a knife selectively movable relative to the jaw members between a retracted position and an extended position, wherein the knife extends at least partially between the jaw members to cut tissue grasped therebetween,
  wherein the knife is coupled to the trigger assembly such that movement of the trigger assembly from the un-actuated position to the actuated position moves the knife from the retracted position to the extended position in both the first and second states of the selector assembly.

13. The surgical instrument according to claim 12, wherein the energizable member and the insulative sleeve define equal travel lengths upon movement of the deployable assembly between the storage position and the deployed position.

14. The surgical instrument according to claim 12, wherein the energizable member and the insulative sleeve define different travel lengths upon movement of the deployable assembly between the storage position and the deployed position.

15. The surgical instrument according to claim 14, wherein the energizable member and the insulative sleeve move together between the respective storage positions thereof and the deployed position of the energizable member and wherein the insulative sleeve thereafter moves further to the deployed position of the insulative sleeve.

16. A surgical instrument, comprising:
  an end effector assembly including first and second jaw members, at least one of the jaw members movable relative to the other between a spaced-apart position and an approximated position for grasping tissue therebetween;
  a trigger assembly movable between an un-actuated position and an actuated position;
  an energizable member selectively movable relative to the jaw members between a first storage position and a first deployed position, wherein at least a portion of the energizable member extends distally from the jaw members in the first deployed position; and
  a selector assembly operably associated with the trigger assembly and the energizable member, the selector assembly transitionable between a first state, wherein the energizable member is decoupled from the trigger assembly, and a second state, wherein the energizable member is coupled to the trigger assembly such that movement of the trigger assembly from the un-actuated position to the actuated position effects movement of the energizable member from the first storage position to the first deployed position, and wherein the selector assembly includes a selector ring, the selector ring rotatable between a first orientation corresponding to the first state, and a second orientation corresponding to the second state.

17. A surgical instrument, comprising:

a housing;

a shaft extending distally from the housing;

an end effector assembly disposed at a distal end of the shaft, the end effector assembly including first and second jaw members, at least one of the jaw members movable relative to the other between a spaced-apart position and an approximated position for grasping tissue therebetween;

a trigger assembly coupled to the housing, the trigger assembly including a trigger movable relative to the housing between an un-actuated position and an actuated position;

a deployable assembly including an energizable member and an insulative sleeve, the deployable assembly selectively movable relative to the jaw members between a storage position and a deployed position; and a selector assembly operably associated with the trigger assembly and the deployable assembly, the selector assembly including a selector member coupled to the housing, the selector member movable relative to the housing between a first position and a second position for transitioning the selector assembly between a first state, wherein the deployable assembly is decoupled from the trigger assembly, and a second state, wherein the deployable assembly is coupled to the trigger assembly such that movement of the trigger assembly from the un-actuated position to the actuated position effects movement of the deployable assembly from the storage position to the deployed position, and wherein the energizable member and the insulative sleeve define equal travel lengths upon movement of the deployable assembly between the storage position and the deployed position.

18. A surgical instrument, comprising:

a housing;

a shaft extending distally from the housing;

an end effector assembly disposed at a distal end of the shaft, the end effector assembly including first and second jaw members, at least one of the jaw members movable relative to the other between a spaced-apart position and an approximated position for grasping tissue therebetween;

a trigger assembly coupled to the housing, the trigger assembly including a trigger movable relative to the housing between an un-actuated position and an actuated position;

a deployable assembly including an energizable member and an insulative sleeve, the deployable assembly selectively movable relative to the jaw members between a storage position and a deployed position; and a selector assembly operably associated with the trigger assembly and the deployable assembly, the selector assembly including a selector member coupled to the housing, the selector member movable relative to the housing between a first position and a second position for transitioning the selector assembly between a first state, wherein the deployable assembly is decoupled from the trigger assembly, and a second state, wherein the deployable assembly is coupled to the trigger assembly such that movement of the trigger assembly from the un-actuated position to the actuated position effects movement of the deployable assembly from the storage position to the deployed position, and wherein the energizable member and the insulative sleeve define different travel lengths upon movement of the deployable assembly between the storage position and the deployed position.

\* \* \* \* \*